(12) United States Patent
Hsieh et al.

(10) Patent No.: US 7,977,406 B2
(45) Date of Patent: Jul. 12, 2011

(54) ENDODONTICS SEALER

(75) Inventors: Kuo-Huang Hsieh, Taipei (TW);
Chun-Pin Lin, Taipei (TW);
Ken-Hsuan Liao, Taipei (TW);
Chung-Yi Lee, Taipei (TW)

(73) Assignee: National Taiwan University, Taipei (TW)

( * ) Notice: Subject to any disclaimer, the term of this patent is extended or adjusted under 35 U.S.C. 154(b) by 391 days.

(21) Appl. No.: 12/339,384

(22) Filed: Dec. 19, 2008

(65) Prior Publication Data
US 2009/0131552 A1 May 21, 2009

Related U.S. Application Data

(63) Continuation-in-part of application No. 11/765,591, filed on Jun. 20, 2007, now abandoned.

(51) Int. Cl.
| | |
|---|---|
| *A61K 6/09* | (2006.01) |
| *A61K 6/02* | (2006.01) |
| *A61K 6/087* | (2006.01) |
| *C08G 18/04* | (2006.01) |
| *C08G 18/42* | (2006.01) |

(52) U.S. Cl. ....... 523/118; 433/224; 433/26; 433/228.1; 522/96; 522/97; 106/35

(58) Field of Classification Search .................. 523/118; 433/224, 226, 228.1; 522/96, 97; 106/35
See application file for complete search history.

(56) References Cited

U.S. PATENT DOCUMENTS

| | | | | |
|---|---|---|---|---|
| 5,263,861 | A * | 11/1993 | Cohen et al. | 433/224 |
| 6,353,041 | B1 * | 3/2002 | Qian | 523/116 |
| 2003/0045599 | A1 * | 3/2003 | Khudyakov et al. | 522/96 |
| 2005/0027033 | A1 * | 2/2005 | Knaack et al. | 523/115 |
| 2005/0107562 | A1 * | 5/2005 | Leberfinger et al. | 528/44 |

OTHER PUBLICATIONS

DESMOPHEN 2001 KS product information; Bayer MaterialScience LLC, Feb. 1997.*

* cited by examiner

*Primary Examiner* — Mark Eashoo
*Assistant Examiner* — Michael Pepitone
(74) *Attorney, Agent, or Firm* — WPAT, PC; Justin King

(57) ABSTRACT

The present invention discloses an endodontic sealer which comprises a urethane-monoacrylate oligomer, a diluting monomer, at least one photo-initiator, at least one thermal-initiator, and a filler, wherein the urethane-monoacrylate oligomer is obtained by firstly reacting the acrylate with the diisocyanate to form an intermediate with only one isocyanate group, and then reacting the intermediate with the polyol to form the desired urethane-monoacrylate oligomer.

15 Claims, 5 Drawing Sheets urethane-monoacrylate urethane-monoacrylate

ENDODONTICS SEALER

CROSS REFERENCE TO RELATED APPLICATIONS

This application is a continuation in part of applicant's earlier application Ser. No. 11/765,591, filed Jun. 20, 2007, now abandoned, which is related to U.S. patent application Ser. No. 11/765,575, filed Jun. 20, 2007, now abandoned.

BACKGROUND OF THE INVENTION

1. Field of the Invention

The present invention is generally related to an endodontic sealer, more specifically, is related to a urethane-monoacrylate resin-based endodontic sealer and the corresponding endodontic obturation material.

2. Description of the Prior Art

The purpose of root canal treatment is to create an end result where the tissues that surround a tooth's root will maintain a healthy status despite the fact that the tooth's nerve has undergone degenerative changes. Root canal treatment occurs in three stages: First comes the diagnosis. Next comes the root canal itself, in which a dentist or an endodentist (a dentist who specializes in treating the inside of the tooth) removes the pulp (and thereby the infection), and cleans the inside of the tooth preparatory to filling it, sometimes applying antibiotics to thwart further infection. A temporary filling is placed at the crown opening. Finally, in a subsequent appointment, a crown is installed to seal the tooth and protect it from further damage or infection.

Root canal obturation involves inserting a filling cone into a root canal and cementing it therein to obturate the canal using a sealer. The canal obturation material consists of a filling cone and a sealer. The common root canal filling cone material is made from gutta-percha or resilon. Root canal obturation involves inserting a filling cone into a root canal and cementing it therein to obturate the canal using a sealer. The canal obturation material consists of a filling cone and a sealer. The common root canal filling cone material is made from gutta-percha or resilon. The gutta-percha was commercialized for first time in 1887 by SS White Company, up to now already 120 years history; the ingredient of the gutta-percha includes a matrix mainly made from gutta-percha, and a filler mainly consists of zinc oxide. Resilon™ was developed by Resilon Research, the research and development team, as a new generation canal obturation material in 2004. The ingredient of Resilon™ includes a resin matrix mainly made from polycarolactone, and a filler primarily contains bioactive glass, ZnO, Tricalcium phosphate and Barium sulfate. The traditional canal obturation material mainly fall into three categories, the first kind is Zinc oxide-eugenol-based, thus has the antibacterial effect and is bio-degradable. However, it shrinks when hardens. The second kind is Calcium hydroxide-based, which is considered to be antibacterial as well as osteogenic cementogenic, but has not been firmly proven. In addition, it depends on dissolution to release the calcium ions and hydroxide ions, inevitably will lead to production of air bubbles and gaps in the obturation system. The third kind is glass ionomer-based; it was claimed to have good dentin bonding, but has been proven not as anticipated. The trend of new-generation canal obturation material is towards polymer-based materials.

The traditional root canal material is inert in nature and will not be absorbed or degraded by living tissue if the root canal is overfilled and the material extends beyond the apex. It has been a challenge for dentists to control the exact amount of the material within the border of the root canal to avoid overfilling. The cold core of the root canal material is not malleable so that it cannot be molded to the canal walls, resulting in poor adherence. In addition, when heated the root canal material cools to body temperature in the root, a uniform contraction takes place further reducing adherence to the root canal walls. Moreover, the filling is a polyisoprene rubber material in nature, which does not have the capability to bond to most dental materials, especially when the root canal sealer is a polymer-based material. Due to poor adherence and bonding, bacteria residential in the root canal can multiply or a leakage may result, causing bacteria to enter the canal from the mouth, which can lead to the persistence of an infection or other complication. Furthermore, still must request in clinical use to seal fills in the medicinal preparation material to mount thickness not be possible to be high in order to fills in root tube slit, as well as shorter polymerization time reduce technique inconvenient. According to the above, it is important to develop a novel set of root canal material which has high biocompatibility, low volume contractive rate, better chemical-bonding ability with dentinal wall and the filling and high mechanical properties.

SUMMARY OF THE INVENTION

In light of the above background, the present invention provides an endodontic sealer.

One of the features of the present invention is to provide an endodontic sealer which comprises a urethane-monoacrylate oligomer, a diluting monomer, at least one photo-initiator, at least one thermal-initiator, and a filler, wherein the urethane-monoacrylate oligomer is obtained by firstly reacting the acrylate with the diisocyanate to form an intermediate with only one isocyanate group, and then reacting the intermediate with the polyol to form the desired urethane-monoacrylate oligomer.

Another feature of the present invention is to provide an endodontic obturation material which comprises a cone material and the above sealer. The cone material is mainly made from a polyurethane composite material, and its physical and chemical properties can be adjusted through varying the kinds and compositions of the diisocyanate and polyol used. The cone material can also be mixed with antibiotic materials to have better performance.

Accordingly, the present invention discloses an endodontic sealer which comprises a photo-curable urethane-monoacrylate oligomer, at least one diluting monomer, at least one photo-initiator, at least one thermal initiator, and a filler.

BRIEF DESCRIPTION OF THE DRAWINGS

The accompanying drawings incorporated in and forming a part of the specification illustrate several aspects of the present invention, and together with the description serve to explain the principles of the disclosure. In the drawings.

DETAILED DESCRIPTION OF THE PREFERRED EMBODIMENTS

Figure 1:
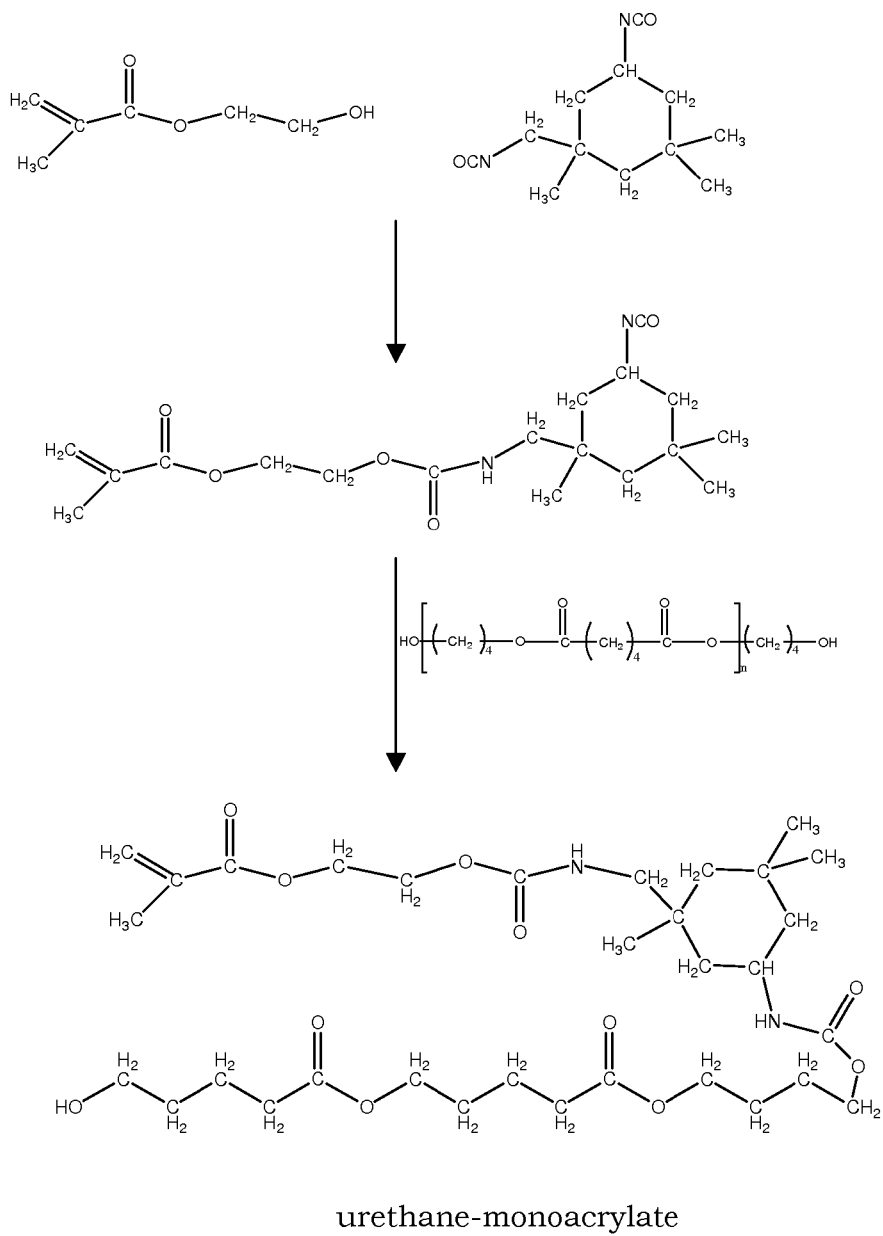
FIG. 1 is a flow chart of the formation process of the urethane-monoacrylate oligomer according to Example 1.

What is probed into the invention is an endodontic sealer. Detail descriptions of the structure and elements will be provided in the following in order to make the invention thoroughly understood. Obviously, the application of the invention is not confined to specific details familiar to those who are skilled in the art. On the other hand, the common structures and elements that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

The first embodiment of the present invention discloses an endodontic sealer comprising a light-curable urethane-monoacrylate oligomer, at least a diluent monomer, a photo-initiator, a thermal initiator, and a filler. The urethane-monoacrylate oligomer synthesis process is as follows: first reacting the acrylate with the diisocyanate to form an intermediate with only one isocyanate group, and then reacting the intermediate with the polyol to form the desired urethane-monoacrylate oligomer. The urethane-monoacrylate oligomer is better selected to be 2-hydroxyethyl methacrylate (HEMA), Hydroxyethyl Acrylate (HEA), Hydroxypropyl Acrylate (HPA). In addition, the filler comprises inorganic materials, preferably HEMA-modified silicon oxide ($SiO_2$) nanoparticles.

The above-mentioned diisocyanate can be aromatic polyisocyanates, alicyclic polyisocyanates or aliphatic polyisocyanates. In detail, the diisocyanate can be selected from the group consisting of the following: (1) aromatic polyisocyanates: tolylene diisocyanate (TDI) (2,4- or 2,6-TDI), diphenylmethane diisocyanate (MDI) (4,4'- or 2,4'-MDI), polymeric MDI, xylylene diisocyanate (XDI), naphthylene diisocyanate (NDI) (usually 1,5-NDI), paraphenylene diisocyanate (PPDI), tetramethylxylylene diisocyanate (TMXDI), tolidine diisocyanate (TODI), 3,3'-dimethoxy-4,4'-biphenylene diisocyanate, etc. (2) alicyclic polyisocyanates: dicyclohexylmethane diisocyanate (HMDI) (4,4'- or 2,4'-HMDI), isophorone diisocyanate (IPDI), isopropylidene-bis-(4-cyclohexylisocyanate) (IPC), hydrogenated xylylene diisocyanate (hydrogenated XDI), cyclohexylene diisocyanate (CHPI) (usually 1,4-CHPI), 1,5-tetrahydonaphthalene diisocyanate, etc. (3) aliphatic polyisocyanates: hexamethylene diisocyanate (HDI), lysine diisocyanate (LDI), tetramethylene diisocyanate, etc.

The above-mentioned polyol can be poly-ester polyol, poly-ether polyol or poly-carbonate polyol. In detail, the polyol can be selected from the group consisting of the following: (1) poly-ester polyol: Polycaprolactone (PCL), Poly(butylene-adipate) glycol (PBA), Poly(ethylene-adipate) glycol (PEA), Poly(ethylene-butylene-adipate) glycol (PEBA), Poly(hexylene-adipate) glycol (PHA); (2) poly-ether polyol: Polyethylene Glycol (PEG), Polypropylene Glycol (PPG), Polytetramethylene Glycol (PTMEG), Polytetramethylene Oxide (PTMO); (3) poly-carbonate polyol: poly(1,3-propanediol carbonate) polyol (PTMC).

The second embodiment of the present invention discloses an endodontic obturation material comprising a cone material and a sealer which is similar to that described in the first embodiment. The cone material comprises a thermoplastic polyurethane and a filler. The thermoplastic polyurethane is formed through reaction of a diisocyanate and a polyol, the diisocyanate comprises one selected from the following group or any combination thereof: (1) aromatic polyisocyanates: tolylene diisocyanate (TDI) (2,4- or 2,6-TDI), diphenylmethane diisocyanate (MDI) (4,4'- or 2,4'-MDI), polymeric MDI, xylylene diisocyanate (XDI), naphthylene diisocyanate (NDI) (usually 1,5-NDI), paraphenylene diisocyanate (PPDI), tetramethylxylylene diisocyanate (TMXDI), tolidine diisocyanate (TODI), 3,3'-dimethoxy-4,4'-biphenylene diisocyanate; (2) alicyclic polyisocyanates: dicyclohexylmethane diisocyanate (HMDI) (4,4'- or 2,4'-HMDI), isophorone diisocyanate (IPDI), isopropylidene-bis-(4-cyclohexylisocyanate)(IPC), hydrogenated xylylene diisocyanate (hydrogenated XDI), cyclohexylene diisocyanate (CHPI) (usually 1,4-CHPI), 1,5-tetrahydonaphthalene diisocyanate; (3) aliphatic polyisocyanates: hexamethylene diisocyanate (HDI), lysine diisocyanate (LDI), tetramethylene diisocyanate.

In addition, the above-mentioned polyol comprises one selected from the group consisting of the following: (1) polyester polyol: Polycaprolactone (PCL), Poly(butylene-adipate) glycol (PBA), Poly(ethylene-adipate) glycol (PEA), Poly(ethylene-butylene-adipate) glycol (PEBA), Poly(hexylene-adipate) glycol (PHA); (2) poly-ether polyol: Polyethylene Glycol (PEG), Polypropylene Glycol (PPG), Polytetramethylene Glycol (PTMEG), Polytetramethylene Oxide (PTMO); (3) poly-carbonate polyol: Poly(1,3-propanediol carbonate) polyol (PTMC). Moreover, the above-mentioned filler preferably comprises zinc oxide (ZnO), fluoroaluminosilicate glass, etc.

EXAMPLE 1

Synthesis of Sealer

This example will introduce various urethane-monoacrylate oligomers and their forming processes as disclosed by this invention. Referring to FIG. 1, the process begins with reacting isophrone Diisocyanate (IPDI) and 2-hydroxyethyl methacrylate (HEMA) with a molar ratio of 1:1 so that the hydroxyl group of HEMA reacts with the isocyanate group of IPDI to form a first intermediate which has, at its two ends, an acrylate group and an isocyanate group, respectively. Then, add polybutyleneadipate (PBA) into the system so that the hydroxyl group of PBA reacts with the isocyanate group of the first intermediate to form a urethane-monoacrylate oligomer which has, at its two ends, an acrylate group and a hydroxyl group, respectively. It is noted that the hydroxyl group of the urethane-monoacrylate oligomer is inactive towards the photo-curing reaction, and is able to be replaced by other functionally equivalent functional groups such as hydrogen atom, hydroxyl group, alkyl group, and aromatic group. It is noted that this example utilizes difunctional or multifunctional acrylate as diluting monomer, such as: 1,6-hexanediol diacrylate (HDDA), tripropylene glycol diacrylate (TPGDA), polyethyleneglycol diacrylate (PEGDA), trimethylolpropane triacrylate (TMPTA), pentaerythritol triacrylate (PETA), and ditrimethylolpropane tetraacrylate (DTMPTA). Take TPGDA diluting monomer for example, this example provided Urethane Acrylate(UA)/TPGDA resin with different weight ratio.

Viscosity Analysis of UA/TPGDA Resin

Viscosities of various polybutyleneadipate (PBA) molecule weights with various TPGDA contents are shown in Table 1. All PBA systems with HDI as diisocyanate are solid so that no viscosity data will be obtained from them. Only PBA with molecule weight 500 (hereinafter named as PBA500) system with IPDI as diisocyanate is available with various TPGDA contents because their low viscosity. Furthermore, the viscosity decreases with the increasing dilute monomer (TPGDA) content. Low viscosity is required for root canal sealer. If the sealer viscosity is too high, it is not convenient for clinical root canal obturating treatment. From Table 1, low viscosity sealer is obtained by using PBA with molecule weight about 500 and UA/TPGDA with weight ratio about 7/3.

TABLE 1

Viscosity of urethane-monoacrylate with various TPGDA contents
Viscosity (cp)

| | UA/TPGDA (by wt.) | | | | | | |
|---|---|---|---|---|---|---|---|
| | 4/6 | 5/5 | 6/4 | 7/3 | 8/2 | 9/1 | Pure |
| PBA 2k | IM | IM | IM | Solid | Solid | Solid | Solid |
| PBA 1k | 247 | 423 | 790 | 2018 | IM | IM | Solid |
| PBA 500 | 127 | 270 | 556 | 1243 | 2919 | >10000 | >10000 |

*IM = immiscible

Another type urethane-acrylate oligomer of this example has an acrylate group at both of its two ends. Starting with the same reactants as mentioned above, the urethane-acrylate oligomer is formed through the following process: firstly, react IPDI and PBA with a molar ratio of 2:1 so that the isocyanate group of IPDI reacts with the hydroxyl group of PBA to form a second intermediate which has an isocyanate group at both of its two ends. Next, react HEMA and the second intermediate with a molar ratio of 2:1 so that the hydroxyl group of HEMA reacts with the isocyanate group of the second intermediate to form the urethane-acrylate oligomer which has an acrylate group at both of its two ends. In practice, after the sealer is inserted into the root canal, the polymer in the deeper portion of the root canal is not easily cured due to insufficient exposure to light. To overcome this, a dual curing mechanism is designed and implemented in this example such that after the insertion of sealer, a 40-second exposure to light is performed to initiate the photo-curing reaction, and the released heat is then absorbed by the uncured polymer, thereby activating a thermal curing process until all the polymer is cured. In addition, this example utilizes DL-camphoro-quinone (CQ) and Ethyl N,N-dimethyl-4-amino-benzoate (EDMAB) with a weight ratio of CQ:EDMAB=1:2 as the photo-initiator, and Azobisisobutyronitrile (AIBN) as the thermal initiator. Moreover, this example utilizes HEMA-modified silicon oxide(SiO$_2$) particles as the filler.

EXAMPLE 2

Photo-curing Depth Analysis

This example investigates the photo-curing depth of the disclosed UA/TPGDA resin(weight ratio 7:3) when mixed with varying amount of filler. The filler comprises HEMA-modified silicon oxide (SiO$_2$) nano-particles. The results is compared with the commercial products Epiphany and EndoRez, as shown in Table 2. As shown, when mixed with 0~40wt % filler, the photo-curing depth of the disclosed UA/TPGDA resin exceeds 10 mm, compared to the 0.5 mm and 0.1 mm for the commercial Epiphany and EndoRez, respectively. This indicates that the disclosed UA/TPGDA resin is superior in transparency, therefore is able to absorb more light.

TABLE 2

Photo-curing depth of UA/TPGDA resin mixed with varying amount of filler

| Amount of HEMA-modified silicon oxide nano-particles (wt. %) | Photo-curing depth (mm) |
|---|---|
| 0 | >10.0 |
| 10 | >10.0 |
| 20 | >10.0 |
| 30 | >10.0 |
| 40 | >10.0 |
| Epiphany | 0.5 |
| EndoRez | 0.1 |

EXAMPLE 3

Flow Property of the Sealer

This example investigates the flow property of the disclosed UA/TPGDA resin (weight ratio 7:3) when mixed with varying amount of filler. The filler comprises HEMA-modified silicon oxide(SiO$_2$) nano-particles. The results is compared with the commercial products Epiphany and EndoRez, as shown in Table 3. As shown, the flow property of the disclosed UA/TPGDA resin is better than the commercial Epiphany and EndoRez. Good flow property will facilitate the insertion of sealer, hence the disclosed UA/TPGDA, with its superior flow property can meet the industrial needs. Viscosity of Epiphany and EndoRez was not available because we did not have enough amounts for testing. So the relationship between flow and viscosity of the UA/TPGDA resin is calculated by Newton's law of viscosity. Detail of the calculation is as explained in Appendix. The equation between viscosity and flow value is shown as below:

$$\mu = 1.0089 \times 10^{-3} \cdot d^{-5}$$

While $\mu$(cp) is the viscosity of the sample, and d (m) is the flow test result value with unit in meter.

TABLE 3

Viscosity and flow property of UA/TPGDA resin mixed with varying amount of filler

| Amount of HEMA-modified silicon oxide nano-particles (wt. %) | Viscosity (cp) | Flow property (mm) |
|---|---|---|
| 0 | 1243 | 61 |
| 10 | 1632 | 59 |
| 20 | 2017 | 57 |
| 30 | 2433 | 56 |
| 40 | 2807 | 54 |
| Epiphany | — | 24 |
| EndoRez | — | 36 |

EXAMPLE 4

Polymerization Contraction Property of the Sealer

Figure 2:
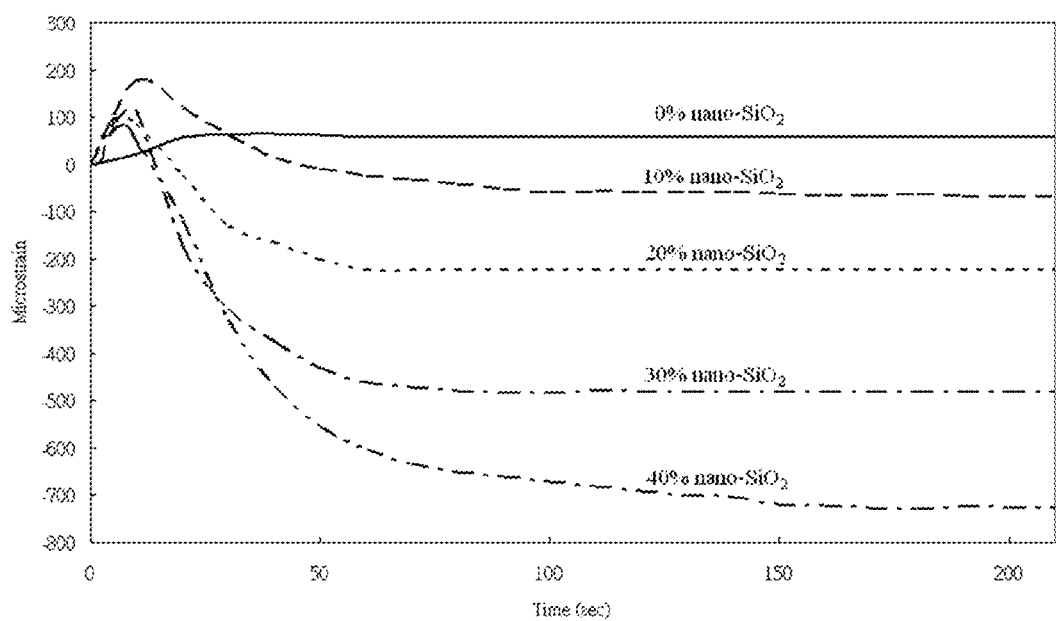
FIG. 2 is an illustration of the polymerization contraction property of the UA/TPGDA resin, when mixed with varying amount of the filler, according to Example 4.

This example investigates the polymerization contraction property of the disclosed UA/TPGDA resin (weight ratio 7:3)

when mixed with varying amount of filler. The filler comprises HEMA-modified silicon oxide ($SiO_2$) nano-particles. The investigation is carried out using the Strain Gauge Method and the result is illustrated in FIG. 2. As shown, the disclosed UA/TPGDA resin has a low contraction percentage during polymerization, and the higher the filler content, the lower the contraction percentage. Polymerization contraction will decrease the tightness of the sealer against the canal wall, hence the disclosed UA/TPGDA with its low contraction percentage can meet the industrial needs.

EXAMPLE 5

Bonding Strength Between the Obturation System and the Canal Wall

Figure 3:
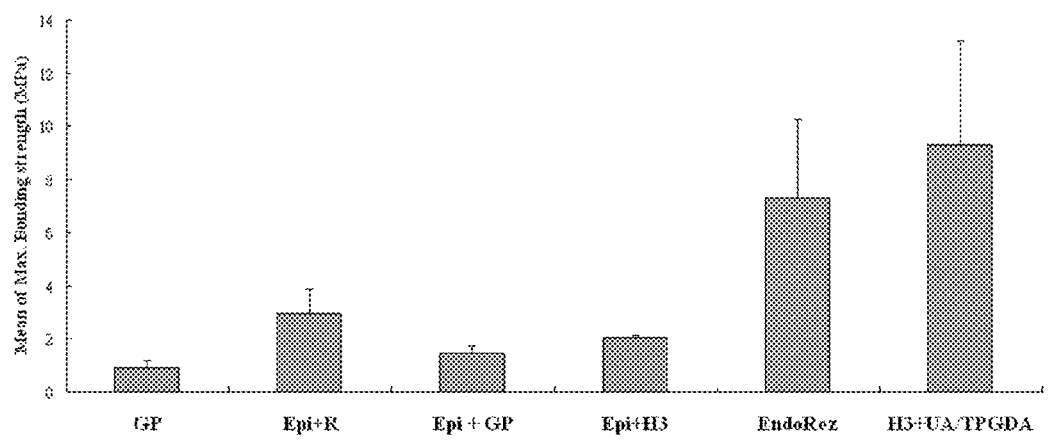
FIG. 3 is a comparison of the bonding strength between the cone material and the sealer according to Example 5.

This example investigates the bonding strength between the polymerized cone material and the sealer disclosed in the present invention. The result is shown in Table 4 and FIG. 3. As shown, when mixed with 40wt % filler, the disclosed UA/TPGDA resin (weight ratio 7:3) together with cone material "H3" makes an endodontic obturation material which displays a superior bonding strength. The filler comprises HEMA-modified silicon oxide nano-particles. Detailed description of the above-mentioned cone material "H3" can be found in the patent application "Polyurethane Composite Material and Application Thereof", U.S. patent application Ser. No. 11/765,575; it is a polyurethane composite material and comprises a thermoplastic polyurethane and a filler.

TABLE 4

Bonding strength between the cone material and the sealer

| Sample (cone material + sealer) | Bonding strength (MPa) |
| --- | --- |
| GP with no sealer | 0.93 ± 0.25 |
| Epiphany + Resilon | 2.94 ± 0.91 |
| Epiphany + gutta-percha | 1.45 ± 0.28 |
| Epiphany + Composite H3 | 2.04 ± 0.10 |
| EndoRez (sealer + point) | 7.28 ± 2.98 |
| UA-based sealer + Composite H3 | 9.29 ± 3.92 |

*UA-based sealer: UA/TPGDA (7/3 by wt.) with 40% HEMA-modified nano-$SiO_2$ as filler As described above, the cone material is a polyurethane composite material and comprises a thermoplastic polyurethane and a filler. The thermoplastic polyurethane is formed through reaction of a polyol, a diisocyanate and a chain extender. The data, as explained in detail herein below, compares the impact of various polyol/diisocyanate/chain extender mole ratio on the mechanical properties of formed polyurethane composite material. The weight ratios of the thermoplastic polyurethane and filler are lower than 5:5, and more preferred to about 3:7. In this example, the polyol is selected to be poly (butylene-adipate) glycol(PBA) and the chain extender is 1,4-Butanediol (1,4-BD). The result of comparison is shown in Table 5.

TABLE 5

Mechanical properties of cone material

| Designations | TPU Composition (Polyol/ Diisocyanate/ Chain extender) | Mechanical Properties | |
| --- | --- | --- | --- |
| | | Tensile Strength (Mpa) | Yang's Modulus (Mpa) |
| Composite H1 | 1/1.60/0.5 | Not-available | Not-available |
| Composite H2 | 1/1.36/0.3 | Not-available | Not-available |
| Composite H3 | 1/1.12/0.1 | 21.8 ± 2.6 | 130.0 ± 18.3 |
| Composite IP1 | 1/1.60/0.5 | Not-available | Not-available |
| Composite IP2 | 1/1.36/0.3 | 0.8 ± 0.3 | 32.1 ± 13.4 |
| Composite IP3 | 1/1.12/0.1 | 15.8 ± 1.9 | 96.2 ± 17.7 |
| Gutta-percha | — | 5.98 ± 1.15 (a) | 78.71 ± 23.41 (a) |
| Resilon | — | 8.09 ± 2.30 (a) | 86.58 ± 42.23 (a) |

As shown in table 2, tensile strength of commercial gutta-percha and resilon is generally less than 10 MPa, and Young's Modulus of gutta-percha and resilon is generally less than 90 MPa. In this example, when the mole ratio of polyol and diisocyanate is 0.88 (polyol: diisocyanate=1:1.12), the sample utilizing IPDI as diisocyanate to form cone material has a tensile strength and Young's Modulus greater than 10 MPa (IP3; 15.8 MPa) and 90 MPa (IP3; 96.2 MPa), respectively. Similarly, when the mole ratio of polyol and diisocyanate is 0.88 (polyol: diisocyanate=1:1.12), the sample utilizing HDI as diisocyanate to form cone material has a tensile strength and Young's Modulus greater than 20 MPa (H3; 21.8 MPa) and 100 MPa (H3; 130.0 MPa), respectively. The preferred mole ratio of polyol and diisocyanate is equal to or more than 0.8. The mechanical properties of root canal material determine the post-treatment tooth tightness and chewing ability, therefore the present invention has a great potential in the application of root canal material.

EXAMPLE 6

SEM Analysis of the Sealer

Figure 4:
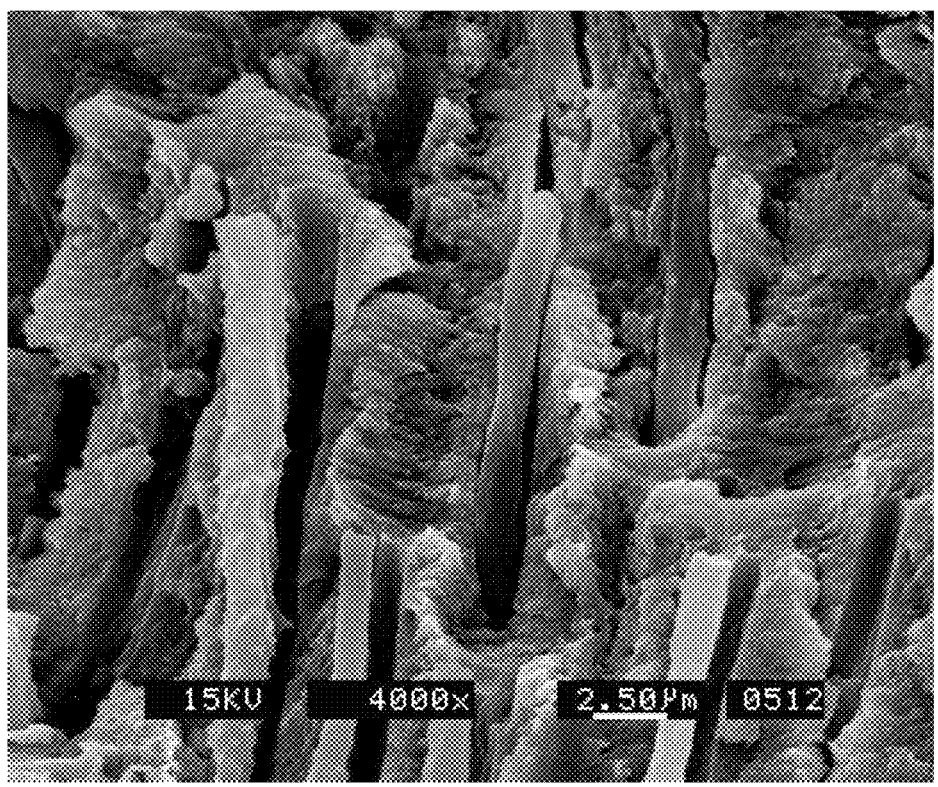
FIG. 4 is an SEM analysis showing a cross sectional view of the root canal after insertion of the disclosed sealer (4000×, sealer contents: UA/TPGDA resin with a weight ratio of 7:3 and mixed with 40 wt % HEMA-modified silicon oxide as filler).

This example uses the scanning electron microscope (SEM) to observe the insertion of the disclosed UA/TPGDA resin(weight ratio 7:3) into the root canal when mixed with 40 wt % filler. The filler comprises HEMA-modified silicon oxide nano-particles. The result is shown is FIG. 4, which is a cross sectional view of the root canal after insertion of the disclosed UA/TPGDA resin. As shown, the disclosed sealer (based on the disclosed UA/TPGDA resin) flowed deep into the root canal and was completely cured into long narrow pieces of polymer.

APPENDIX

Figure 5:
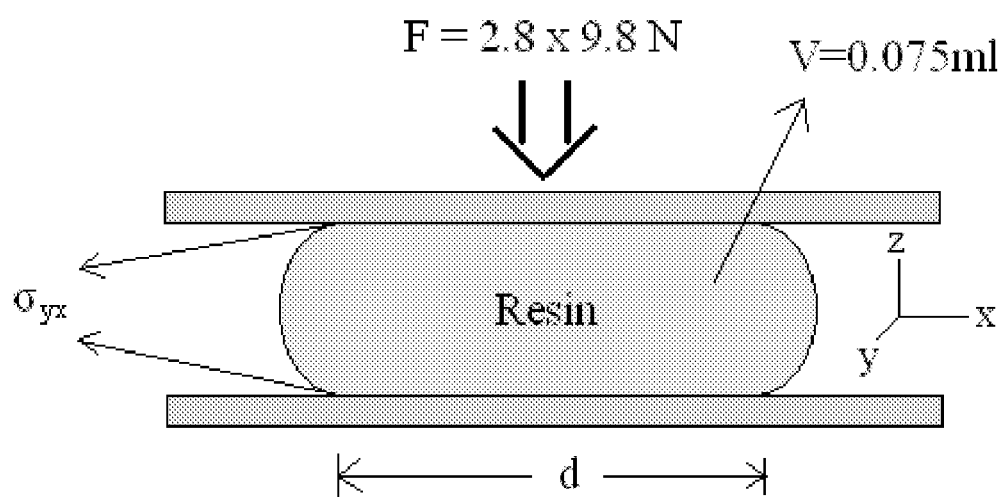
FIG. 5 is a sketch of calculation of relationship between viscosity and flow value

Viscosity presents the ability of for sealer to flow into dentin tube. Lower viscosity makes sealer flow into tube more easily. Precise physical meaning of viscosity is the measure of the fluid's resistance to deform under shear stress. Flow property of sealer is highly related to sealer's viscosity. The relationship between flow and viscosity was calculated as below. The sketch illustrates with FIG. 5. It is assumed that the load is reduced by the shear stress between resin and glass surface. So the equation is as equation 1. While $\zeta_{zx}$ is the shear stress in z-axis which is resulted from x-axis moving fluid, and F is the load including applied load and weight of the glass plate, and A ($m^2$) is the area of the resin after applying load for 600 sec.

$$2 \cdot \zeta_{zx} = F/A \quad (1)$$

It is also assumed that the resin is a fluid with constant viscosity so that the shear stress was proportional to the velocity gradient. The $\zeta_{zx}$ can be presented as below while $\mu$ is the viscosity with unit in cp.

$$\zeta_{zx} = \mu \cdot \frac{\varphi Vx}{\varphi z} \quad (2)$$

The average velocity gradient was considered here. So the velocity gradient can be transformed to:

$$\frac{\varphi Vx}{\varphi z} = \frac{(d/2t)}{(V/2A)} \quad (3)$$

While d (m) is the flow result; t (sec) is the load applying time. The applying time is 600 sec, the area of the resin is $\pi d^2/4$, and the load is 2.8·9.8 Nt. So the equation 1 can be transformed as below.

$$\mu = 1.0089 \times 10^{-3} \cdot d^{-5} \quad (4)$$

Obviously many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

The invention claimed is:

1. An endodontic sealer, comprising:
   a light-curable urethane-monoacrylate oligomer, wherein the urethane-monoacrylate oligomer has, at its two ends, an acrylate group and a hydroxyl group respectively, the urethane-monoacrylate oligomer is a reaction product of (a) isophorone diisocyanate, (b) acrylate having hydroxyl group, and (c) polybutyleneadipate (PBA) with molecule weight about 500;
   at least one difunctional or multifunctional acrylate diluting monomer; and
   at least one initiator.

2. The endodontic sealer according to claim 1, further comprising a filler.

3. The endodontic sealer according to claim 1, wherein the acrylate having hydroxyl group is selected from the group consisting of 2-hydroxyethyl methacrylate(HEMA), hydroxyethyl acrylate(HEA), hydroxypropyl acrylate (HPA), and any combination thereof.

4. The endodontic sealer according to claim 1, wherein the difunctional or multifunctional acrylate diluting monomer is selected from the group consisting of 1,6-heanediol diacrylate (HDDA), tripropyleneglycol diacrylate (TPGDA), polyethyleneglycol diacrylate (PEGDA), trimethylolpropane triacrylate (TMPTA), pentaerythritol triacrylate (PETA), ditrimethylolpropane tetraacrylate (DTMPTA), and any combination thereof.

5. The endodontic sealer according to claim 1, wherein the weight ratio of urethane-monoacrylate oligomer/diluting monomer is about 7/3.

6. An endodontic obturation material, comprising:
   a cone material, comprising a thermoplastic polyurethane and a filler;
   and an endodontic sealer as cited in claim 1.

7. The endodontic obturation material according to claim 6, wherein the weight ratio of the thermoplastic polyurethane and the filler is equal to or less than 0.5.

8. The endodontic obturation material according to claim 6, wherein the weight ratio of the thermoplastic polyurethane and the filler is about 3:7.

9. The endodontic obturation material according to claim 6, having a bonding strength equal to or greater than 8 MPa.

10. The endodontic obturation material according to claim 6, wherein the thermoplastic polyurethane is a reaction product of (a) diisocyanate comprising isophorone diisocyanate (IPDI) or hexamethylene diisocyanate (HDI), (b) polybutyleneadipate (PBA), and (c) chain extender.

11. The endodontic obturation material according to claim 10, wherein the mole ratio of PBA and the diisocyanate is equal to or more than 0.8.

12. The endodontic obturation material according to claim 6, wherein the tensile strength of the cone material is equal to or more than 10 MPa.

13. The endodontic obturation material according to claim 6, wherein the tensile strength of the cone material is equal to or more than 20 MPa.

14. The endodontic obturation material according to claim 6, wherein the Young's Modulus of the cone material is equal to or more than 90 MPa.

15. The endodontic obturation material according to claim 6, wherein the Young's Modulus of the cone material is equal to or more than 100 MPa.

* * * * *